US006881705B2

(12) United States Patent
Garnier et al.

(10) Patent No.: US 6,881,705 B2
(45) Date of Patent: Apr. 19, 2005

(54) FUNGICIDAL COMPOSITION AND USE OF THIS COMPOSITION FOR CONTROLLING PLANT DISEASES

(75) Inventors: Alain Joseph Jean Florimond Garnier, Turnhout (BE); Luc Rosalia Michaël Verbruggen, Kasterlee (BE); Richard Milling, Lyons (FR); Patrice Duvert, Lyons (FR)

(73) Assignee: Bayer Cropscience S.A. (FR)

( * ) Notice: Subject to any disclaimer, the term of this patent is extended or adjusted under 35 U.S.C. 154(b) by 0 days.

(21) Appl. No.: 10/485,338

(22) PCT Filed: Jul. 24, 2002

(86) PCT No.: PCT/EP02/09425

§ 371 (c)(1),
(2), (4) Date: Jan. 30, 2004

(87) PCT Pub. No.: WO03/011030

PCT Pub. Date: Feb. 13, 2003

(65) Prior Publication Data

US 2004/0167144 A1 Aug. 26, 2004

(30) Foreign Application Priority Data

Aug. 1, 2001 (FR) ............................................. 01 10301

(51) Int. Cl.$^7$ ................................................ A01N 53/54
(52) U.S. Cl. ...................................................... 504/136
(58) Field of Search ........................... 504/136; 424/405

(56) References Cited

U.S. PATENT DOCUMENTS 6,413,973 B1 * 7/2002 Walter et al. ............ 514/266.3

FOREIGN PATENT DOCUMENTS

FR        2692108        12/1998

* cited by examiner

Primary Examiner—Alton Pryor
(74) Attorney, Agent, or Firm—Ostrolenk, Faber, Gerb & Soffen, LLP

(57) ABSTRACT

The present invention relates to a fungicidal composition comprising at least one fungicidal compound of the family of anilinopyrimidines and imazalil, and the use of such a composition combining these active compounds for controlling plant diseases or the phytopathogenic fungi present or capable of appearing on plants.

14 Claims, No Drawings

FUNGICIDAL COMPOSITION AND USE OF THIS COMPOSITION FOR CONTROLLING PLANT DISEASES

CROSS REFERENCE TO RELATED APPLICATION

The present application is a 35 U.S.C. § 371 national phase conversion of PCT/EP02/09425, filed Jul. 24, 2002, which claims priority of French Application No. 0110301 filed Aug. 1, 2001.

The present invention relates to a fungicidal composition comprising at least one fungicidal compound of the family of anilinopyrimidines and imazalil, and the use of such a composition combining these active compounds for controlling plant diseases or the phytopathogenic fungi present or capable of appearing on plants.

Fungicidal compounds of the family of anilinopyrimidines are known from the literature and in particular from the book entitled *The Electronic Pesticide Manual* version 1.1 (by British Crop Protection Council, published by Clive Tomlin); this book also describes imazalil for its fungicidal properties.

Moreover, French Patent Application No. 2 692 108 which essentially relates to mixtures based on pyrimethanil and numerous other compounds gives a list of more than eleven types of families of fungicidal compounds and of more than 70 candidate compounds for the mixture; among this systematic list of compounds, only 23 mixtures have led to laboratory experimentation, none under open field conditions. Thus, even if the pyrimethanil and imazalil mixture is mentioned by this document, this mixture was not prepared and even less tested.

However, it is still desirable to improve the products which can be used by the farmer for controlling fungicidal diseases of plants and in particular of crops.

It is also still desirable to improve the fungicidal products used for treating fruit.

In addition, while imazalil may be used as a preventive and curative treatment, this curative effect remains limited over time.

It is also still desirable to reduce the doses of chemical products applied to plants or fruit, in particular by reducing the applied doses of the products.

It is finally still desirable to increase the range of available antifungal products in order to find among them those best suited to specific uses.

It is also still advantageous to have antifungal means of treating fruit, in particular after harvest, and which can be reused or recycled during their application.

Likewise, it is very advantageous to have a means of protecting fruits during their preservation, their storage, their transport and up to their marketing or their consumption.

It has also become essential to be able to have antifungal means of treatment which limit or avoid phenomena of resistance of phytopathogenic organisms.

It is also advantageous to have such products which have the broadest possible activity spectrum.

To the numerous problems which have just been disclosed, there are added most often those linked to the protection of the environment, environmental problems to which the users of fungicidal active ingredients, as well as consumers of products obtained from these crops, are increasingly sensitive.

Another difficulty relating to the use of numerous fungicidal substances lies in the accumulation of several of the problems which have just been disclosed. It is indeed even more difficult to solve the problems posed when they accumulate because the solutions which can be envisaged are sometimes antinomical or even antagonistic.

A first object of the present invention consists in providing fungicidal compositions possessing a broad activity spectrum, that is to say possessing a substantial activity on a larger number of phytopathogenic fungi than the number of phytopathogenic fungi treated with known compositions.

A second object of the invention consists in providing fungicidal compositions possessing both a preventive effect and a curative effect, in particular an improved curative effect compared with the fungicidal compositions currently used.

Another object of the present invention consists in providing fungicidal compositions which can effectively control fungal strains resistant to known fungicidal compositions.

Another aim of the present invention is to provide fungicidal compositions which are effective at significantly lower doses compared with the doses currently applied.

Another object of the present invention consists in providing fungicidal compositions.

Another object of the present invention consists in providing a fungicidal composition possessing preventive, curative, eradicant and antisporulant properties.

Another object of the present invention is to provide a composition useful to control plant phytopathogenic organisms after harvest, notably on fruit.

Other objects of the invention will appear in the disclosure of the invention which is presented in the remainder of the present description.

Surprisingly, it has been discovered that all of these objects may be achieved completely or in part using the fungicidal compositions which are the subject of the present invention.

The present invention also proposes achieving all or some of the objectives which have just been mentioned.

The present invention relates to a composition comprising at least one fungicidal compound of the family of anilinopyrimidines and imazalil.

Among the anilinopyrimidine-type fungicidal compounds, those advantageously suitable for the composition according to the invention are cyprodinil, mepanipyrim and pyrimethanil.

The preferred combination of active ingredients according to the present invention is the association of pyrimethanil and imazalil.

References to methods for preparing such anilinopyrimidine compounds and imazalil will be found in the book cited above.

In the composition according to the invention, the ratio of the quantities of compound of the family of anilinopyrimidines and imazalil generally ranges from 0.0005 to 250, preferably from 0.05 to 10.

However, the ratio of these compounds ranging from 0.1 to 10, preferably from 0.15 to 6, still more preferably from 0.25 to 4, have proved even more advantageous.

Usually, the compositions according to the invention comprise between 0.00001 and 100%, preferably between 0.001 and 80%, of active compounds, whether these compounds are combined, or whether they are in the form of two active ingredients used separately.

Unless otherwise stated, the proportions and percentages used or described throughout the present description and in the claims which will follow are proportions or percentages by weight.

For their use in practice, the active substances of the composition according to the invention are rarely used alone.

Thus, for their use, these active ingredients are usually combined with a solid or liquid carrier which can be used in particular in the agricultural field, and optionally with at least one surfactant and/or one or more auxiliary agents.

In particular, as carriers, there may be used inert and customary carriers; likewise, as surfactant, there may be used the customary surfactants in the field of formulation of compositions, which are intended for agricultural use, in particular for the treatment or protection of crops such as those of the present invention.

According to another embodiment of the present invention, the various fungicidal compositions according to the invention which have been described up until now may also be in the form of tank mixes.

These fungicidal compositions in the form of tank mixes are usually in the form of dilute fungicidal compositions.

Most often, these so-called tank mix fungicidal compositions are mixed in the reservoir of the application device.

Usually, the fungicidal compounds used in the compositions according to the invention are therefore combined with one or more carriers and/or one or more substances useful for their formulation. Thus, where appropriate, the compositions according to the invention may comprise up to 99% of carrier and/or up to 25% of one or more surfactants and/or up to 25% of one or more formulating agents.

In the present disclosure, the term carrier designates a natural or synthetic, organic or inorganic material with which the active ingredient(s) are in the compositions according to the invention, in particular to facilitate their application to a plant, a fruit or alternatively to seeds or to the soil.

This carrier is therefore generally inert and should most often be acceptable in agriculture, in particular by the treated plant or by the fruit of this plant in the broad sense.

As examples of solid carriers which can be used, there may be mentioned natural or synthetic silicates, resins, waxes, fine powders or granules of clay, in particular kaolinic clay, diatomaceous earth, bentonite or acidic clay, synthetic silicon oxide hydrate, talcs, ceramics, other minerals including sericite, quartz, sulphur, activated charcoal, calcium carbonate, hydrated silica, or alternatively industrial fertilizers such as ammonium sulphate, ammonium phosphate, ammonium nitrate, urea or ammonium chloride.

As examples of liquid carriers which can be used, there may be mentioned water, alcohols and in particular methanol or ethanol, ketones and in particular acetone, methyl ethyl ketone or cyclohexanone, petroleum fractions, aromatic hydrocarbons including benzene, toluene, xylene, ethylbenzene or methylnaphthalene, nonaromatic hydrocarbons including hexane, cyclohexane, kerosene or gas oil, liquefied gas, esters including ethyl acetate and butyl acetate, nitriles including acetonitrile and isobutyronitrile, ethers including diisopropyl ether or dioxane, amides including N,N-dimethylformamide or N,N-dimethylacetamide, halogenated hydrocarbons including dichloromethane, trichloroethane or carbon tetrachloride, dimethyl sulphoxide, vegetable oils including soybean oil or cottonseed oil.

The surfactant(s) may be emulsifying, dispersing or wetting agents of the ionic or nonionic type.

It is possible, for example, to mention salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols, in particular alkylphenols or arylphenols, salts of sulphosuccinic acid esters, derivatives of taurine, in particular alkyl taurates, phosphoric esters of polyoxyethylated alcohols or phenols; it is also possible to mention most particularly alkyl sulphonate salts, alkylaryl sulphonates, alkylaryl ethers, polyoxyethylenic derivatives thereof, polyethylene glycol ethers, polyalcohol esters, derivatives of sugars, alcohols and the like.

The presence of at least one surfactant is generally essential when at least one of the active ingredients and/or the inert carrier are not soluble, in particular in water, in the case where the carrier agent for the application is water.

In the compositions according to the invention, it is also possible to combine with the active compounds all sorts of other ingredients or agents such as, for example, protective colloids, adhesives, thickening agents, thixotropic agents, penetrating agents, stabilizing agents including isopropyl hydrogen phosphate, 2,6-di-tert-butyl-4-methylphenol, 2-tert-butyl4-methoxyphenol and 3-tert-butyl-4-methoxyphenol, vegetable or mineral oils, fatty acids or esters thereof, sequestering agents, dispersing agents including casein, gelatin, saccharides and in particular starch powder, gum arabic, certain derivatives of cellulose or alginic acid, derivatives of lignin, bentonite, synthetic polymers soluble in water, in particular polyvinyl alcohol, polyvinylpyrrolidone, polyacrylic acids, and the like, as well as other active ingredients known for their pesticidal, in particular insecticidal or fungicidal, properties; or for their plant growth promoting properties, in particular fertilizers; or for their insect or plant growth regulating properties.

Thus, the fungicidal compositions according to the invention may take fairly diverse forms, in particular they may be in solid or liquid forms.

More generally, the compositions according to the invention may take numerous forms of formulations; thus, these compositions comprising the active compounds may be used in the form of an aerosol dispenser; suspension of capsules; cold fogging concentrate; dustable powder; emulsifiable concentrate; aqueous/aqueous type emulsion; oil/inverse type emulsion; encapsulated granule; fine granule; suspension concentrate for seed treatment; compressed gas; gas generating product; granule; hot fogging concentrate; macrogranule; microgranule; oil-dispersible powder, oil miscible suspension concentrate; oil-miscible liquid; paste; plant rodlet; powder for dry seed treatment; seed coated with a pesticide; smoke candle; smoke cartridge; smoke generator; smoke pellet; smoke rodlet; smoke tablet; smoke tin; soluble concentrate; soluble powder; solution for seed treatment; suspension concentrate (=flowable concentrate); tracking powder; ultra low volume liquid; ultra low volume suspension; vapour releasing product; water-dispersible granules or tablets; water dispersible powder for slurry treatment; water-soluble granules or tablets; water-soluble powder for seed treatment; wettable powder; as well as possible mixtures, associations or combinations of these various forms.

Most often, for dustable powder or dispersion type formulations, the content of active compounds may be up to 100%; likewise, for formulations in the form of granules, in particular those obtained by extrusion, compacting, impregnation of a granular support, or granulation using a powder, the content of fungicidal compounds in these granules according to the invention is most often between 0.5 and 80%.

The fungicidal compositions according to the invention, which are termed concentrated compositions, comprise the active compounds in the form of emulsifiable or soluble concentrates, comprise most often from 25 to 100% of these active ingredients; the emulsions or solutions ready for application containing, for their part, from 0.00001 to 20% of active ingredients.

It goes without saying that the expression active ingredients should be understood throughout the present disclosure as, where appropriate, an active ingredient or a fungicidal compound alone, but also a combination of these two active ingredients.

In addition to the solvent, the emulsifiable concentrates may contain, when necessary, 2 to 20% of appropriate additives such as stabilizing agents, surfactants, penetrating agents, corrosion inhibitors, colouring agents or adhesives mentioned above.

The compositions according to the invention in the form of suspension concentrates, which can also be applied by spraying, are prepared so as to obtain a stable, fluid product which does not become deposited; they usually contain from 2 to 75% of active ingredients, from 0.5 to 15% of surfactants, from 0.1 to 10% of thixotropic agents, from 0 to 10% of appropriate additives, such as antifoaming agents, corrosion inhibitors, stabilizing agents, penetrating agents and adhesives; and, as carrier, water or an organic liquid in which the active ingredient(s) are sparingly soluble or insoluble, or alternatively mixtures of several of these solvents, organic or otherwise.

Some solid organic substances or inorganic salts may be dissolved in the carrier to retard or prevent sedimentation; or alternatively such substances may be used as antifreeze for water.

The fungicidal compositions according to the invention which take the form of wettable powders or flo-dusts are usually prepared so that they contain from 20 to 95% of active ingredients.

Moreover, they usually contain, in addition to a solid carrier, from 0 to 5% of a wetting agent, from 3 to 10% of a dispersing agent, and, where appropriate, from 0 to 10% of one or more stabilizing agents and/or other additives, such as penetrating agents, adhesives, or anticaking agents, colouring agents and the like.

To obtain these flo-dusts or wettable powders, the active ingredient(s) are intimately mixed in appropriate mixers with additional substances, and they are ground with mills or other appropriate grinders. Flo-dusts are then obtained whose wettability and suspension are particularly advantageous; they can be suspended with water at any desired concentration.

Rather than wettable powders, it is possible to prepare fungicidal compositions according to the invention which are in the form of pastes.

The conditions and modalities for the preparation and use of these pastes are similar to those of wettable powders or flo-dusts.

As already stated, aqueous dispersions and emulsions, for example the fungicidal compositions obtained by diluting with water a wettable powder or an emulsifiable concentrate according to the invention, are included in the general context of the present invention.

The emulsions may be of the water-in-oil or oil-in-water type and they may have a thick or fairly thick consistency.

In addition to the fungicidal compounds of the family of anilinopyrimidines and imazalil, the composition according to the invention may also comprise other active compounds and in particular one or more active compounds useful for protecting plants against pests.

Among such active compounds, the composition according to the invention may therefore comprise one or more insecticidal, herbicidal or fungicidal compounds or growth regulating compounds.

Among the additional insecticidal, acaricidal or nematicidal active ingredients which may be used alone or in combination with other active ingredients, in particular pesticides, in the composition according to the invention, there may be mentioned abamectin; acephate; acetamiprid; oleic acid; acrinathrin; aldicarb; alanycarb; allethrin [(1r)-isomers]; α-cypermethrin; amitraz; azadirachtin; azamethiphos; azinphos-ethyl; azinphos-methyl; bacillus thurigiensi; bendiocarb; benfuracarb; bensultap; beta-cyfluthrin; beta-cypermethrin; bifenthrin; bioallathrin; bioallethrin (isomer s-cyclopentenyl); bioresmethrin; borax; buprofezin; butocarboxim; butoxycarboxim; piperonyl butoxide; cadusafos; carbaryl; carbofuran; carbosulphan; cartap; cartap hydrochloride; chlordane; chlorethoxyfos; chlorfenapyr; chlorfenvinphos; chlorfluazuron; chlormephos; chloropicrin; chlorpyrifos; chlorpyrifos-methyl; mercury(I) chloride; coumaphos; cryolite; cryomazine; cyanophos; calcium cyanide; sodium cyanide; cyclopro-thrin; cyfluthrin; cyhalothrin; cypermethrin; cyphenothrin [(1r)-trans-isomers]; dazomet; ddt; deltamethrin; demeton-s-methyl; diafenthiuron; diazinon; ethylene dibromide; ethylene dichloride; dichlorvos; dicrotophos; diflubenzuron; dimethoate; dimethylvinphos; diofenolan; disulfoton; dnoc; dpx-jw062 and dp; empenthrin [(ez)-(1r)-isomers]; endosulfan; ent 8184; epn; esfenvalerate; ethiofencarb; ethion; ethiprole having the chemical name 5-amino-3-cyano-1-(2,6-dichloro-4-trifluoromethylphenyl)-4-ethylsulphinylpyrazole; ethoprophos; etofenprox; etrimfos; famphur; fenitrothion; fenobucarb; fenoxycarb; fenpropathrin; fenthion; fenvalerate; fipronil; flucycloxuron; flucythrinate; flufenoxuron; flufenprox; flumethrin; fluofenprox; sodium fluoride; sulphuryl fluoride; fonofos; formetanate; formetanate hydrochloride; formothion; furathiocarb; gamma-hch; gy-81; halofenozide; heptachlor; heptenophos; hexaflumuron; sodium hexafluorosilicate; tar oils; petroleum; hydramethylnon; hydrogen cyanide; hydroprene; imidacloprid; imiprothin; isazofos; isofenphos; isoprocarb; methyl isothiocyanal; isoxathion; lambda-cyhalothrin; pentachlorophenyl laurate; lufenuron; malathion; mb-599; mecarbam; methacrifos; methamidophos; methidathion; methiocarb; methomyl; methoprene; methoxychlor; metolcarb; mevinphos; milbemectin; monocrotophos; naled; nicotine; nitenpyram; nithiazine; novaluron; omethoate; oxamyl; oxydemeton-methyl; paecilomyces fumosoroseus; parathion; parathion-methyl; pentachlorophenol; sodium pentachlorophenoxide; permethrin; phenothrin [(1r)-trans-isomer]; phenthoate; phorate; phosalone; phosmet; phosphamidon; phosphine; aluminium phosphide; magnesium phosphide; zinc phosphide; phoxim; pirimicarb; pirimiphos-ethyl; pirimiphos-methyl; calcium polysulphide; prallethrin; profenofos; propaphos; propetamphos; propoxur; prothiofos; pyraclofos; pyrethrins (chrysanthemates, pyrethrates, pyrethrum); pyretrozine; pyridaben; pyridaphenthion; pyrimidifen; pyriproxyfen; quinalphos; resmethrin; rh-2485; rotenone; ru 15525; silafluofen; sulcofuron-sodium; sulfotep; sulfuramide; sulprofos; α-fluvalinate; tebufenozide; tebupirimfos; teflubenzuron; tefluthrin; temephos; terbufos; tetrachlorvinphos; tetramethrin; tetramethrin [(1r)-isomers]; theta-cypermethrin; thiocyclam; thicyclam hydrogen oxalate; thiodicarb; thiofanox; thiometon; tralomethrin; transfluthrin; triazamate; triazophos; trichlorfon; triflumuron; trimethacarb; vamidothion; xde-105; xmc; xylylcarb; zeta-cypermethrin; zxi 8901; the compound whose chemical name is 3-acetyl-5-amino-1-[2,6-dichloro-4-(trifluoromethyl)phenyl]-4-methylsulphinylpyrazole.

Among the additional fungicidal active ingredients which may be used alone or in combination with other active ingredients, in particular pesticides, in the composition according to the invention, there may be mentioned 2-phenylphenol; 8-hydroxyquinoline sulphate; ac 382042; ampelomyces quisqualis; azaconazole; azoxystrobin; bacillui subtilis; benalaxyl; benomyl; biphenyl; bitertanol; blasticidin-s; Bordeaux mixture; borax; bromuconazole; bupirimate; calboxin; calcium polysulphide; captafol; captan; carbendazim; carpropamid (ktu 3616); cga 279202; chinomethionat; chlorothalonil; chlozolinate; copper hydroxide; copper naphthenate; copper oxychloride; copper sulphate; copper oxide; cymoxanil; cyproconazole; cyprodinil; dazomet; debacarb; dichlofluanid; dichlomezine; dichlorophen; diclocymet; dicloran; diethofencarb; difenoconazole; difenzoquat; difenzoquat metilsulphate; diflumetorim; dimethirimol; dimethomorph; diniconazole; diniconazole-m; dinobuton; dinocap; diphenylamine; dithianon; dodemorph; dodemorph acetate; dodine; dodine free base; edifenphos; epoxiconazole (bas 480f); ethasulfocarb; ethirimol; etridiazole; famoxadone; fenamidone; fenarimol; fenbuconazole; fenfin; fenfuram; fenhexamid; fenpiclonil; fenpropidin; fenpropimorph; fentin acetate; fentin hydroxide; ferbam; ferimzone; fluazinam; fludioxonil; fluoroimide; fluquinconazole; flusilazole; flusulfamide; flutolanil; flutriafol; folpet; formaldehyde; fosetyl; fosetyl-aluminium; fuberidazole; furalaxyl; fusarium oxysporum; gliocladium virens; guazatine; guazatine acetates; gy-81; hexachlorobenzene; hexaconazole; hymexazol; icia 0858; ikf-916; imazalil; imazalil sulphate; imibenconazole; iminoctadine; iminoctadine triacetate; iminoctadine tris[albesilate]; ipconazole; iprobenfos; iprodione; iprovalicarb; kasugamycin; kasugamycin hydrochloride hydrate; kresomix-methyl; mancopper; mancozeb; maneb; mepanipyrim; mepronil; mercury(II) chloride; mercury(II) oxide; mercury(I) chloride; metalaxyl; metalaxyl-m; metam; metam-sodium; metconazole; methasulfocarb; methyl isothiocyanate; metiram; metominostrobin (ssf-126); mon65500; myclotbutanil; nabam; naphthenic acid; natamycin; nickel bis (dimethyldithiocarbamate); nitrothal-isopropyl; nuarimol; octhilinone; ofurace; oleic acid (fafty acids); oxadixyl; oxine-copper; oxycarboxin; penconazole; pencycuron; pentachlorophenol; pentachlorophenyl laurate; perfurazoate; phenylmercury acetate; phlebiopsis gigantea; phthalide; piperalin; polyoxine b; polyoxines; polyoxorim; potassium hydroxyquinoline sulphate; probenazole; prochloraz; procymidone; propamocarb; propamocarb hydrochloride; propiconazole; propineb; pyrazophos; pyributicarb; pyrifenox; pyrimethanil; pyroquilon; quinoxyfen; quintozene; rh-7281; sec-butylamine; sodium 2-phenylphenoxide; sodium pentachlorophenoxide; spiroxamine (kwg 4168); streptomyces griseoviridis; sulphur; tar oils; tebuconazole; tecnazene; tetraconazole; thiabendazole; thifluzamide; thiophanate-methyl; thiram; tolclofos-methyl; tolylfluanid; triadimefon; triadimenol; triazoxide; trichoderma harzianum; tricyclazole; tridemorph; triflumizole; triforine; triticonazole; validamycin; vinclozolin; zinc naphthenate; zineb; ziram; the compounds having the chemical name (e,e)-2-(2-(1-(1-(2-pyridyl)propyloxyimino)-1-cyclopropylmethyloxymethyl)phenyl)-3-methoxy-propenoate de and 3-(3,5-dichlorophenyl)-4-chloropyrazole.

According to another equally advantageous aspect, the present invention also relates to a method for the curative or preventive control of phytopathogenic organisms of plants, such a method according to the invention is based on the use of at least one composition according to the invention.

Among the procedures or methods of treatment and/or protection according to the invention, those which are used for the treatment and/or protection of crops are preferred, and among such methods or procedures, those for the protection of fruit, in particular after harvest, are most particularly preferred.

The said use of the methods according to the invention may be carried out according to various forms and in particular using a fairly large variety of modes of application, but also according to various techniques of application, or alternatively for the protection of various types, varieties or families of vegetables or plants, or alternatively for combating or controlling various types of phytopathogenic organisms.

As regards the various modes of application usefully employed during the methods according to the invention, simultaneous, separate, alternate or sequential modes of application are in particular possible.

Nevertheless, most often, the modes of application useful during the methods according to the invention and which are preferred consist of modes of simultaneously applying the active compounds.

However, a relatively advantageous variant of the method according to the invention uses an alternate mode of application of the active compounds.

Another mode of application useful for carrying out the methods according to the invention relates to the sequential application of the fungicidal compounds; such a sequential mode of application may in particular take the form of several applications of at least one anilinopyrimidine compound, followed by several applications of imazalil.

Quite obviously, a reverse sequential mode of application consisting in several applications of imazalil, followed by several applications of anilinopyrimidine compound also forms part of the methods of the present invention.

The various variants of carrying out the methods according to the invention which have just been described may also be combined or associated, completely or partially, with each other.

Persons skilled in the art will easily know how to determine the associations or combinations of modes of application according to the invention which are best suited to the use of the active compounds which they envisage.

In addition to the various embodiments of the methods according to the invention which have just been described, the said methods can also use a fairly large number of application techniques; thus, as said techniques, there may be mentioned in particular dusting, dipping, spraying, smoking or fogging, and the like.

During the application of the active compounds of the composition according to the invention by dipping, in particular of fruit, the solution used advantageously comprises from 0.01 to 1% of active ingredients, preferably from 0.02 to 0.8%, and still more preferably from 0.03 to 0.6%.

Other variants of the modes of application useful for the methods according to the invention exist, particularly depending on the part(s) of the plant or vegetable which are treated or which are to be treated.

Thus, the methods according to the invention may be carried out for the treatment or protection of plant propagation material or seeds, in particular grain seeds, tubers or rhizomes; for the treatment of roots, or for the treatment of the stems or leaves of the plants; as well as for the treatment of the roots, or alternatively of the fruit or other parts of the plant which possess a substantial economic or agronomic value.

Furthermore, the said methods according to the invention may be carried out for the treatment of plants at numerous stages of their development, in particular for the treatment of the seeds, seedlings or seedlings for transplantation or plants for transplantation, or alternatively plants, fruit or harvests.

Among the crops advantageously treated according to the present invention, there may be mentioned pome fruit, such as apples and pears, citrus fruit, such as oranges, lemons, limes, mandarins, grapefruit, stone fruit, such as peaches, plums, nectarines, cherries, apricots, grapes, in particular table grapes, kiwis, bananas and plantains, strawberries, tomatoes, melons and pineapples.

A class of diseases advantageously treated using the present invention may be given per crop:

Pome fruit (apples, pears): *Penicillium expansum, Gloeosporium* sp., *Botrytis cinerea, Monilinia fructigena, Mucor* sp., Citrus fruit (oranges, lemons, limes, mandarins, grapefruit): *Penicillium expensum, Penicillium digitatum, Geotrichum candidum, Phomopsis citri, Diplodia natalensis, Colletotrichum gloeosporiodes, Alternaria citri,*

Stone fruit (peaches, plums, nectarines, cherries, apricots): *Botrytis cinerea, Monilinia* sp. (*M. laxa, fructicola*), *Alternaria alternata, Colletotrichum gloeosporioides, Penicillium expansum, Cladosporium herbarum, Rhizopus stolonifer* and *Rhizopus oryzae,*

(Table) grapes: *Botrytis cinerea, Aspergillus niger, Penicillium digitatum, Penicillium italicum, Rhizopus stolonifer, alternaria alternata,*

Kiwis: *Botrytis cinerea,*

Bananas, plantains, skin disease (*Colletotrichum musae*), diseases of the crown (*Fusarium semitectum, Pusarium monlilforme, Fusarium paledo-roseum, Acremonium* sp., *Botryodiplodia theo-bromae, Seratocystis paradoxa, Colletotrichum musae, Nigrospora sphaerica*), Strawberries: *Botrytis cinerea, Colletotrichum* sp., *Gnomonia fructicola, Mucor* sp., Tomatoes: *Botrytis cinerea, Alternaria alternata,*

Melons: *Botrytis cinerea, Alternaria solani, Alternaria alternata, Fusarium* sp. (*oxysporum, roseum, solani*), *Colletotrichum gloeosporioides, Penicillium* sp., *Phomopsis* sp., Pineapples: *Ceratocystis paradoxa.*

An additional aspect of the present invention relates to an use of at least one fungicidal anilinopyrimidine compound, in particular cyprodinil, mepanipyrim or pyrimethanil, and of imazalil in controlling fungi by simultaneous or sequential.

It goes without saying that the different variants or embodiments which may be envisaged both of the compositions and of the methods of treatment and/or protection according to the invention form an integral part of the present invention; it being possible for the said different variants, moreover, to be combined or associated with each other without as a result departing either from the spirit or from the scope of the said invention.

In the same manner, the different aspects of the present invention which have just been described may be combined or associated with each other without as a result departing either from the spirit or from the scope of the said invention.

The examples which follow will allow better illustration of the various aspects of the present invention, in particular of the aspects relating to the compositions and to the methods according to the invention using the said fungicidal compositions. However, these examples do not in any way limit the scope of the present invention.

EXAMPLE 1

This example gives an illustration of the efficacy of a composition according to the invention for controlling *Geotrichum candidum*, this trial was carried out in vitro.

The fungicidal compositions are used in solution at the doses detailed in Table 1.

These fungicidal compositions are used in the form of active ingredients previously dissolved in DMSO and then incorporated into a PDA (Potato Dextrose Agar) medium in superfusion at the doses previously described in an amount of 6 µl of fungicidal solution+1 000 µl of PDA per well of 15 mm in diameter of a microtitre plate (4 repeats/product).

1 day later, a microdrop of an aqueous suspension of *Geotrichum candidum* spores, supplemented with 400 ppm of Tween 20, is brought to the surface of each well of the microtitre plate.

The cultures are then incubated at 22° C., 60% relative humidity, under subdued light until the control culture (without fungicide) has covered the entire surface of the well.

The diameter of each colony is then measured and, in comparison with the untreated control, a percentage efficacy is calculated using the following formula:

(diameter of the control−diameter of the trial)/diameter of the control×100.

The results are presented in Table 1 below:

TABLE 1

| | Radial growth of the fungus (mm) | Efficacy (%) |
|---|---|---|
| Control | 15 | / |
| Imazalil at 60 ppm | 14 | 7 |
| Pyrimethanil at 60 ppm | 15 | 0 |
| Pyrimethanil + imazalil at 60 + 60 ppm | 6 | 59 |

Each fungicidal compound, taken in isolation, did not make it possible to control the growth of the fungus whereas the combination provided a significant level of control.

EXAMPLE 2

This example proposes to give an illustration of the efficacy of a composition according to the invention for combating Gloeosporium spp. on apples, this trial was carried out in vivo.

The fungicidal compositions are used in solution at the doses detailed in Table 2.

Apples of the Golden variety, untreated after harvest, are treated by sprinkling a fungicidal solution up to the run-off limit at the doses described in Table 2 of results (8 apples per product).

6 hours later, the fruit are inoculated by sprinkling an aqueous suspension at 150 000 spores/ml of Gloeosporium spp. obtained from a preculture on PDA medium. This inoculation by sprinkling is carried out up to the run-off limit.

The fruit are then stored in the dark at 20° C., 100% relative humidity and the scores for the disease start 3 weeks later, for a period of 2 weeks.

The number of fruit affected by rot are counted and, in comparison with the untreated control, a percentage efficacy is calculated using the following formula:

(diameter of the control−diameter of the trial)/diameter of the control×100.

The results are presented in Table 2 below:

TABLE 2

|  | Efficacy (%) |
| --- | --- |
| Control | / |
| Pyrimethanil at 75 ppm | 14.9 |
| Imazalil at 375 ppm | −29.2 |
| Pyrimethanil + imazalil at 75 + 300 ppm | 77.7 |

Again, each fungicide, taken in isolation, did not make it possible to control the growth of the fungus whereas the combination provided a significant level of control.

What is claimed is:

1. A method for the treatment of phytopathogenic organisms of plants or plant parts comprising contacting said plants or plant parts with a composition consisting essentially of at least one fungicidal compound of the family of anilinopyrimidines and imazalil wherrein said anilinopyrimidines are selected from cyprodinil, mepanipyrim and pyrimethanil.

2. The method of claim 1 wherein the plant part is a fruit.

3. The method of claim 2 carried out after harvest.

4. The method of claim 1 wherein the plants or plant parts are dipped in a solution of the composition.

5. The method of claim 4 wherein the plants or plant parts are dipped in a solution comprising from 0.01 to 1% of the composition.

6. The method of claim 2 wherein the fruit is selected from the group consisting of pome fruit, citrus fruit, stone fruit, grapes, kiwis, bananas, plantains, strawberries, tomatoes, melons, and pineapples.

7. The method of claim 3 wherein the fruit is selected from the group consisting of pome fruit, citrus fruit, stone fruit, grapes, kiwis, bananas, plantains, strawberries, tomatoes, melons, and pineapples.

8. The method of claim 4 wherein the plant parts is a fruit selected from the group consisting of pome fruit, citrus fruit, stone fruit, grapes, kiwis, bananas, plantains, strawberries, tomatoes, melons, and pineapples.

9. The method of claim 5 protecting wherein the plant parts is a fruit selected from the group consisting of pome fruit, citrus fruit, stone fruit, grapes, kiwis, bananas, plantains, strawberries, tomatoes, melons, and pineapples.

10. A composition consisting essentially of:

(A) at least one fungicidal compound of the family of anilinopyrimidines selected from the group consisting of cyprodinil, mepanipyrim, and pyrimethanil;

(B) imazalil; and (C) up to 99% of carrier and/or up to 25% of one or more surfactants and/or up to 25% of one or more formulating agents;

wherein the ratio of the quantities of (A) and (B) ranges from 0.05 to 10.

11. The composition of claim 10 wherein the anilinopyrimidine is pyrimethanil.

12. A method for the treatment of phytopathogenic organisms of fruit comprising contacting said fruit with a composition consisting essentially of:

(A) at least one fungicidal compound of the family of anilinopyrimidines selected from the group consisting of cyprodinil, mepanipyrim, and pyrimethanil;

(B) imazalil; and (C) up to 99% of carrier and/or up to 25% of one or more surfactants and/or up to 25% of one or more formulating agents;

wherein the ratio of the quantities or (A) and (B) ranges from 0.05 to 10;

wherein said method is carried out after harvest; and wherein the fruit is dipped in a solution comprising from 0.01 to 1% of the composition.

13. The method of claim 12 wherein anilinopyrimidine is pyrimethanil.

14. The method of claim 13 wherein the fruit is selected from the group consisting of pome fruit, citrus fruit, stone fruit, grapes, kiwis, bananas, plantains, strawberries, tomatoes, melons, and pineapples.

* * * * *